US006139534A

United States Patent [19]

Niedospial, Jr. et al.

[11] Patent Number: 6,139,534

[45] Date of Patent: Oct. 31, 2000

[54] VIAL ACCESS ADAPTER

[75] Inventors: John J. Niedospial, Jr., Burlington, N.J.; Mark E. Gabbard; Timothy J. Gabbard, both of Salisbury, Md.

[73] Assignee: Bracco Diagnostics, Inc., Princeton, N.J.

[21] Appl. No.: 09/489,619

[22] Filed: Jan. 24, 2000

[51] Int. Cl.[7] ........ A61B 19/00

[52] U.S. Cl. ........ 604/411; 604/403; 604/414

[58] Field of Search ........ 604/126, 403, 604/405, 406, 411, 414, 415, 905; 215/247, 249, 270, 274, 320, 355, DIG. 3

[56] References Cited

U.S. PATENT DOCUMENTS

| | | | |
|---|---|---|---|
| 3,359,977 | 12/1967 | Burke . | |
| 3,608,550 | 9/1971 | Stawski . | |
| 3,783,895 | 1/1974 | Weichselbaum . | |
| 4,211,588 | 7/1980 | Raines . | |
| 4,262,671 | 4/1981 | Kersten . | |
| 4,505,709 | 3/1985 | Froning et al. . | |
| 4,588,403 | 5/1986 | Weiss et al. | 604/411 |
| 4,655,763 | 4/1987 | Malcolm et al. . | |
| 4,787,898 | 11/1988 | Raines . | |
| 4,822,351 | 4/1989 | Purcell | 604/411 |
| 4,834,744 | 5/1989 | Ritson | 604/411 |
| 4,857,068 | 8/1989 | Kahn | 604/405 |
| 4,959,053 | 9/1990 | Jang | 604/127 |
| 4,997,429 | 3/1991 | Dickerhoff et al. | 604/411 |
| 5,041,105 | 8/1991 | D'Alo et al. | 604/411 |
| 5,232,109 | 8/1993 | Tirrell et al. | 215/247 |
| 5,358,501 | 10/1994 | Meyer . | |
| 5,445,630 | 8/1995 | Richmond | 604/411 |
| 5,636,660 | 6/1997 | Pfleiderer et al. . | |

*Primary Examiner*—John G. Weiss
*Assistant Examiner*—David J. Cho
*Attorney, Agent, or Firm*—Imre Balogh

[57] ABSTRACT

A vial access adapter for withdrawal of a medical fluid contained in a vial which includes a vial access adapter body having a circular top wall with a plurality of vent holes, a circular second wall spaced from the top wall, and a cylindrical side wall which walls define a chamber for holding an anti-bacterial filter. A first spike centrally located in the vial access adapter body extends through the top wall, chamber, and bottom wall, with one end extending above the top wall terminating in a threaded luer connector, while the other end terminates in a sharp point. A flow channel extends through the first spike designed for withdrawal of the medical fluid from the vial. A second spike positioned parallel to the first spike extends from the second wall, one end of which extends into the chamber, and the other end terminates in a sharp point. A flow channel extends through the second spike designed for air flow from the chamber into the vial. An elastomeric membrane positioned within the threaded luer connector seals the opening in the vial access adapter. Preferably the elastomeric membrane is of M-shaped configuration capable of flexing under pressure and of re-sealing itself after being pierced by a luer connector or a syringe equipped with a luer connector.

10 Claims, 10 Drawing Sheets

VIAL ACCESS ADAPTER

BACKGROUND OF THE INVENTION

1. Field of the Invention

This invention relates to a vial access adapter connectable to a vial which contains a medical fluid therein and is closed by an elastomeric stopper, wherein the vial access adapter is provided with a dual spike, one for withdrawing the medical fluid from the vial, and the other for simultaneous entry of air into the vial.

2. Reported Developments

Vials made of glass or polymeric materials, the walls of which are non-collapsible, require an air inlet when medical fluid is withdrawn therefrom to prevent the formation of vacuum therein. Typically, vials containing a medical fluid are closed by rubber stoppers which are pierced by a dual spike having a medical fluid passage and an air inlet passage, therein. The air inlet passage contains a filter to prevent entry of particulate matter or bacteria into the vials during the medicament withdrawal process.

The prior art has provided devices comprising a liquid flow passage and an air flow passage, such as disclosed, for example, in U.S. Pat. Nos. 3,359,977, 3,608,550, 3,783,895, 4,262,671, 4,505,709, 4,588,403, 4,787,898, 5,358,501, and 5,636,660. These inventions have advanced the prior art by providing convenient adapters and transfer devices connectable to containers of medical fluids.

In addition to providing in a vial access adapter a dual spike for withdrawing a medical fluid from a vial and simultaneously introducing filtered atmospheric air into the vial, the present invention also provides an elastomeric seal positioned in the fluid passage flow of the dual spike for hermetically sealing the fluid flow passage. In a preferred embodiment the elastomeric seal is of an M-shaped configuration through which the medical fluid can be accessed repeatedly. After each withdrawal of the desired amount of the medical fluid the elastomeric seal reseals itself thereby preventing contamination of the medical fluid by air-born particles, such as dust and bacteria.

A further improvement in the present invention over the prior art is the spatial configuration of the medical fluid access spike which, on positioning of the vial access adapter over a vial having a rubber stopper, penetrates the rubber stopper and just clears the bottom surface of the rubber stopper. This spatial configuration allows essentially complete withdrawal of the medical fluid contained in the vial.

SUMMARY OF THE INVENTION

In accordance with the present invention, there is provided a vial access adapter for use with a glass vial or a rigid or semi-rigid polymeric vial containing a liquid medicament, diagnostic agent, or nutritional formulation therein. The vial access adapter body comprises:

a horizontal top wall having a plurality of vent holes therein;

a horizontal second wall spaced parallel from the horizontal top wall;

a cylindrical side wall integral with the horizontal top wall and the horizontal second wall enclosing a chamber therebetween and extending downward from the horizontal second wall forming a skirt and terminating in a bottom rim;

a first spike centrally located in the vial access adapter body having a top portion extending above the horizontal wall and terminating in an externally threaded luer connector, and a bottom portion extending downward and terminating in a sharp point;

a fluid flow channel in the first spike designed for carrying the liquid medicament;

a second spike positioned parallel to the first spike extending downward from the horizontal second wall and terminating in a sharp point;

an air flow channel in the second spike designed for air flow from the chamber between the horizontal top wall and the horizontal second wall into the vial during withdrawal of the liquid medicament from the vial; and an elastomeric membrane within the luer connector for sealing the fluid flow channel.

Preferably, the elastomeric membrane reseals itself upon repeated penetration by an external luer connector and allows repeated withdrawal of the liquid medicament from the vial without risk of contamination from atmospheric environment.

DETAILED DESCRIPTION OF THE INVENTION

Figure 1:
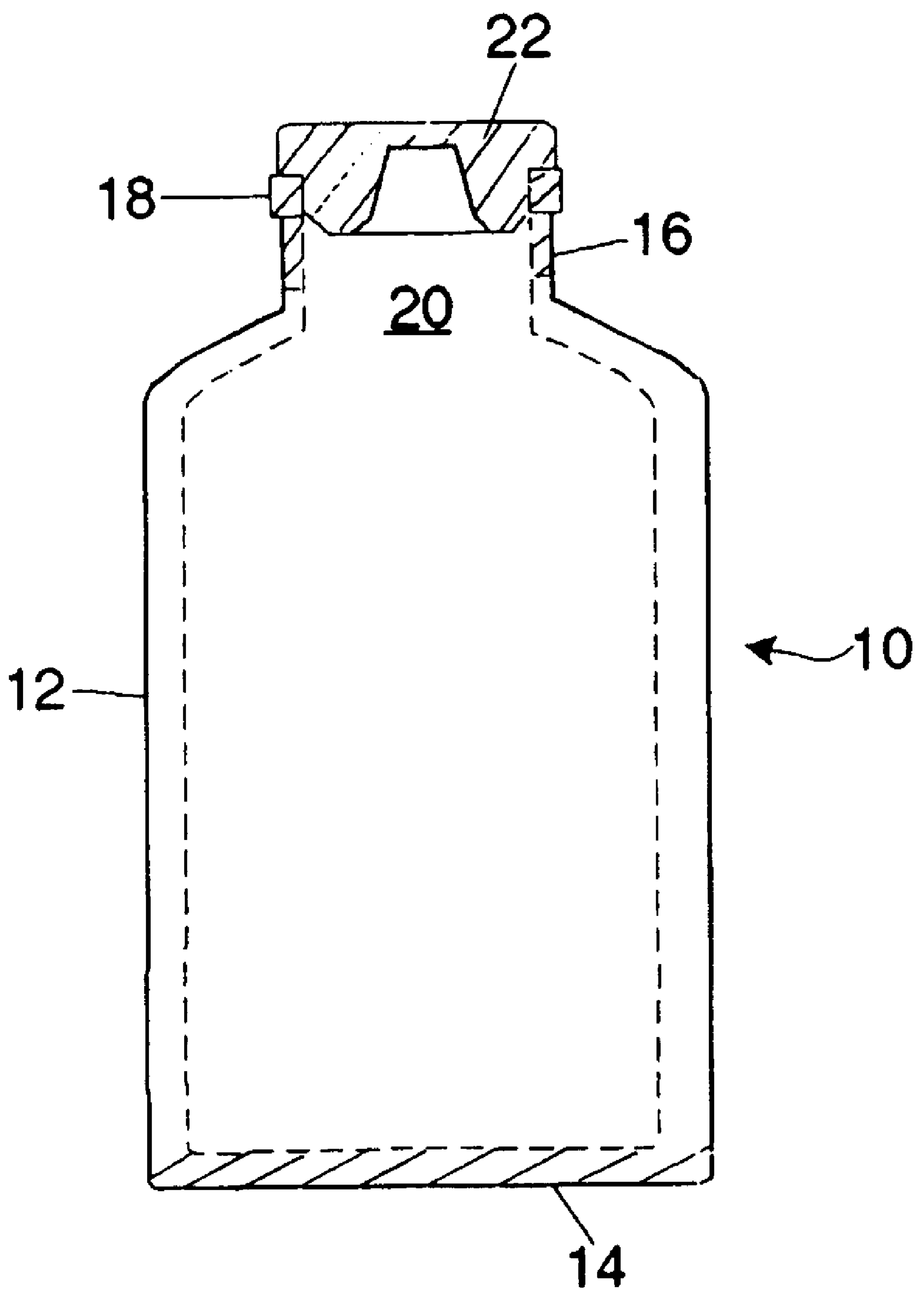
FIG. 1 is a cross-section of a typical vial used in conjunction with the vial access adapter of the present invention.

The vial access adapter of the present invention is used in conjunction with containers such as vials containing a fluid medicament therein, such as parenteral solutions and diagnostic media. Referring to the drawings, FIG. 1 shows the cross-section of vial 10 in an upright position having: a cylindrical side wall 12, a flat bottom portion 14 so that it may be placed in normal upright position on any flat surface, and a constricted neck portion 16 terminating in a rim 18. The neck portion and rim define an open area 20 closed by stopper 22 hermetically sealing the content of the vial. Typically, the stopper is held in the vial by a metal band (not shown).

Figure 2:
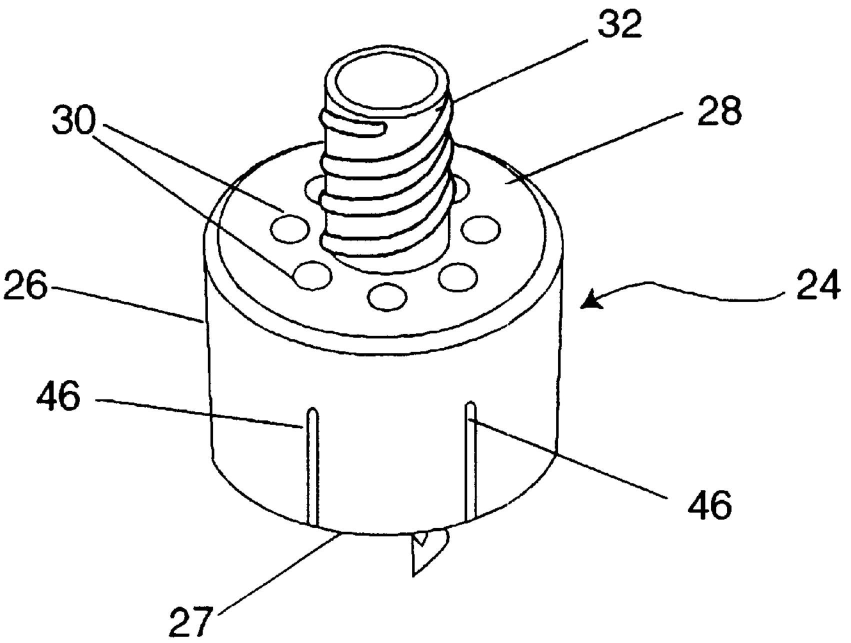
FIG. 2 is a perspective view of the vial access adapter showing the cylindrical side wall, flat top portion with vent holes, and threaded luer connector means rising above the flat top portion.
Figure 3:
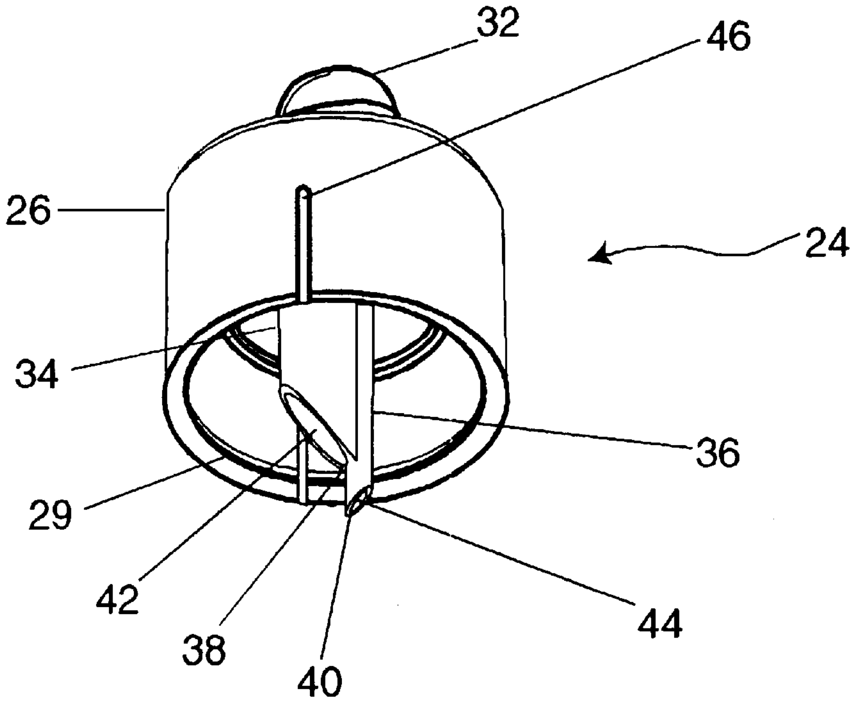
FIG. 3 is a another perspective view of the vial access adapter showing the cylindrical side wall, and the dual spike terminating in piercing sharp points.

The vial access adapter, generally designated by the numeral 24 and shown in perspective views in FIGS. 2 and 3, comprises: a cylindrical side wall 26 terminating in a rim 27; a flat, horizontal top wall 28 having vent holes 30 therein; threaded luer connector means 32 projecting vertically above the horizontal top wall 28; and a dual spike 34 and 36 terminating in sharp points 38 and 40 extending parallel to each other, and having flow passages therein 42 and 44, one being designed for passage of medicament, and the other being designed for passage of air. Cylindrical side wall 26 of the vial access adapter 24 is preferably provided with a plurality of slots 46 to facilitate the positioning of the vial access adapter onto vial 10 by a snap-on motion. In order to securely hold the vial access adapter on the vial, rim 27 of cylindrical sidewall 26 is provided with protuberance 29 projecting towards dual spike 34 and 36. Protuberance 29 engages the neck portion 16 just below rim portion 18 of vial 10.

Figure 4:
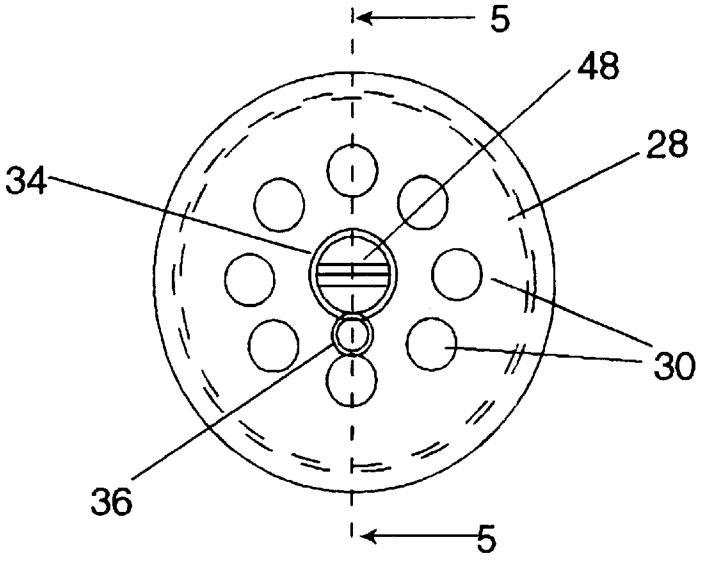
FIG. 4 is a top plan view of the vial access adapter.
Figure 5:
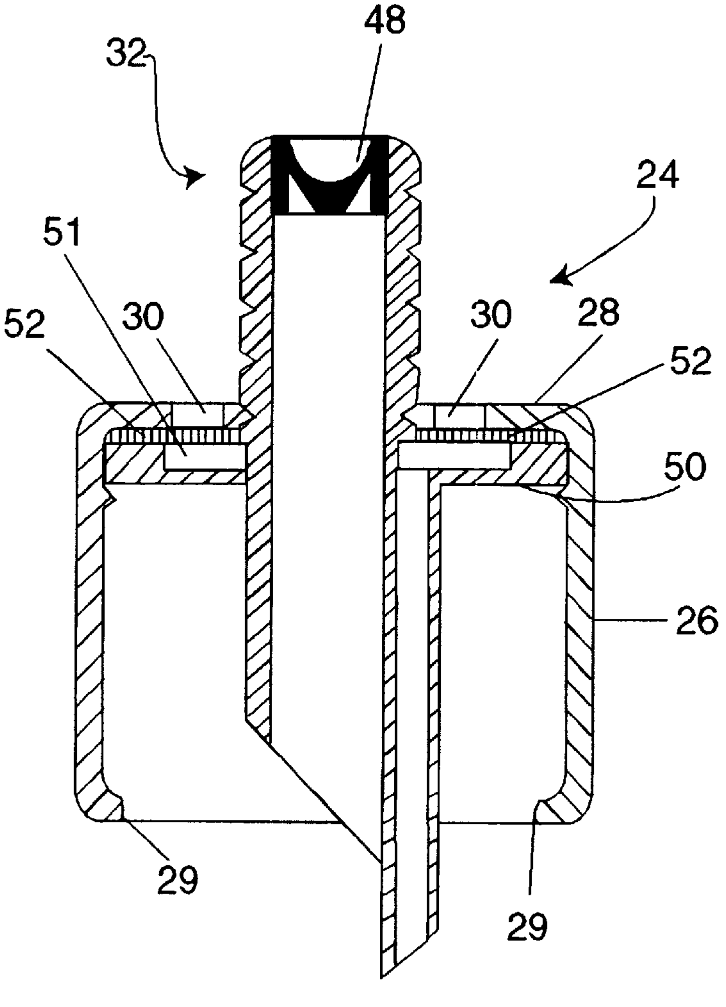
FIG. 5 is a cross-sectional view of the vial access adapter, having an M-shaped member therein, taken along the line 5–5 of FIG. 4.
Figure 5A:
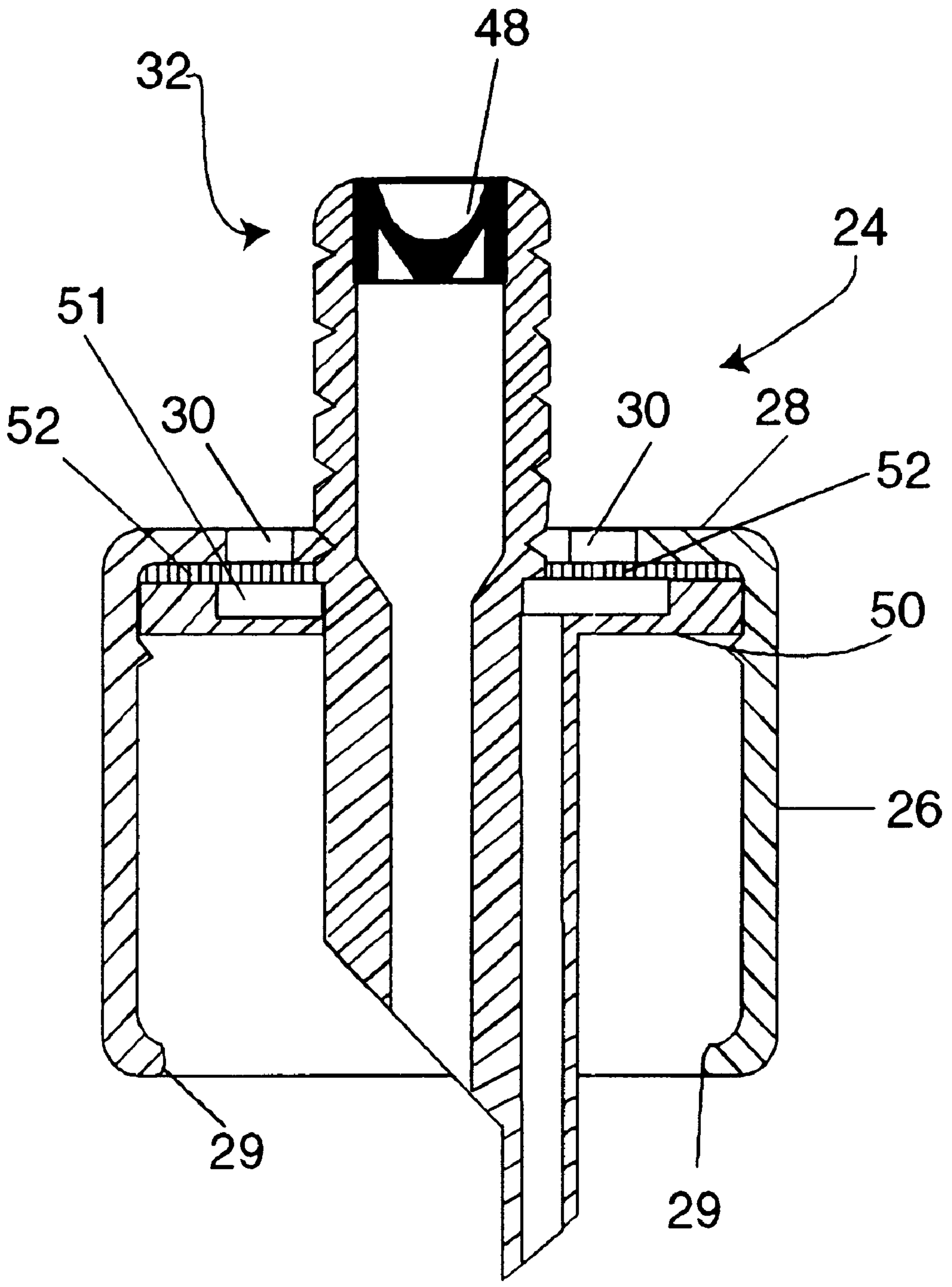
FIG. 5A is a cross-sectional view of the vial access adapter wherein the lower portion of the fluid flow channel has a reduced diameter.

Reference is now made to FIGS. 4 and 5. FIG. 4 shows a top plan view of the vial access adapter and FIG. 5 shows a cross-sectional view of the vial access adapter taken along the line 5—5 of FIG. 4.

In FIG. 4 there are shown: eight vent holes 30 in the flat, horizontal top wall 28, dual spike 34 and 36, and an elastomeric seal 48 positioned inside the threaded luer connector means.

As best seen in FIG. 5, the vial access adapter 24 further comprises an internal second wall 50 which is parallel to the flat, horizontal top wall 28 and is spaced therefrom. Flat, horizontal top wall 28, internal second wall 50, and cylindrical sidewall 26 enclose a chamber 51 therebetween designed to hold a filter 52. The filter is an anti-microbial filter known in the art, such as Whatman Grade HCO1, USP Class 6.

The anti-microbial filter is a circular mat of randomly oriented fibers bound together with a polymeric material, such as a polyester elastomers, ethylene methacrylate, ethylene vinyl acetate, ethylene vinyl alcohol, polyethylene and polypropylene treated with an anti-bacterial agent. The randomly oriented fibers may be made of nylon, cellulose, rayon and polyester.

One of the dual spikes 34 is adapted to carry liquid medicament from vial 10. This spike is integral with the threaded luer connector means 32 and passes through the flat, horizontal top wall 28, and internal second wall 50. When the vial access adapter is assembled with vial 10 and pierces stopper 22, sharp point 38 just clears the bottom surface of stopper 22 to reach the liquid medicament contained in the vial. In use, when the vial is turned upside-down and connected to the vial access adapter, this positioning of the sharp point 38 just below the bottom surface of the stopper allows for maximum amount of withdrawal of medicament from the vial.

The other of the dual spike 36 runs parallel to spike 34, however it only runs from below chamber 51 and is connected to internal second wall 50 and terminates in sharp point 40. It extends into the vial somewhat below sharp point 38 of first spike 34 so that atmospheric air can be introduced into the vial even when the content of the vial is at a minimum volume.

Figure 5B:
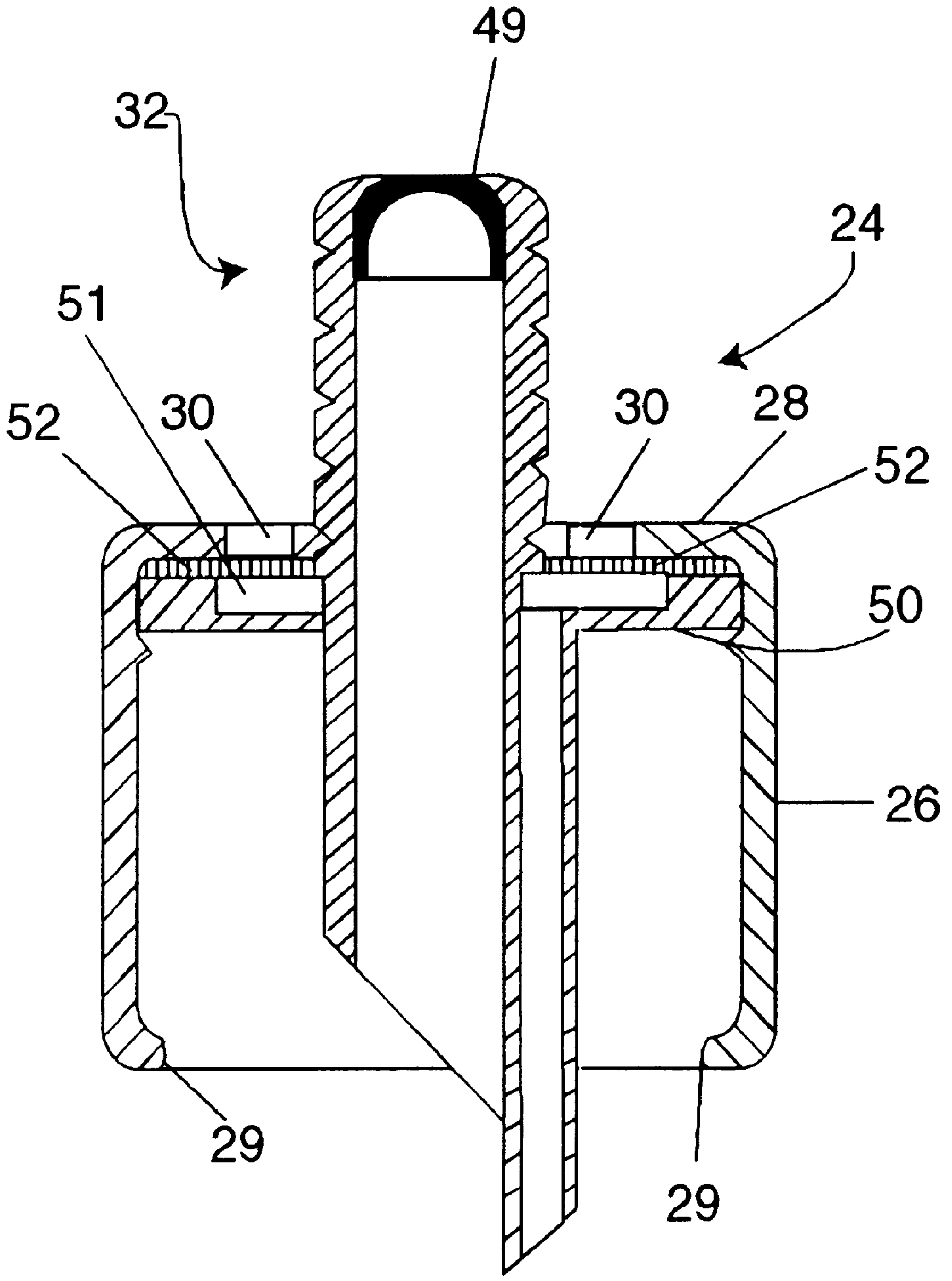
FIG. 5B is a cross-sectional view of the vial access adapter wherein the membrane is of an inverted U-shaped configuration.

The vial access adapter can be used without a seal within the threaded luer connector means 32. Preferably, however, a seal is used to prevent entry of atmospheric air when the vial access adapter is placed on the vial containing a medicament. The seal can be a horizontal, flat elastomeric membrane, or an inverted U-shaped membrane 49 as shown in FIG. 5B, which can be ruptured by a luer connector. Most preferably, the seal is an M-shaped elastomeric seal or membrane capable oi resealing itself after one or more puncture by a luer connector.

The M-shaped elastomeric seal or membrane 48 is of inert, gas-impermeable polymeric material capable of flexing under pressure. It preferably has a thickness of from about 0.001 mm to about 1.00 mm and a durometer of from about 25 to about 80 Shore A. It is capable of being ruptured by a twisting motion of a luer connector. The configuration of the elastomeric membrane is M-shaped having vertical leg portions and a top surface resembling a cup shape. Suitable elastomeric materials for constructing the diaphragm include:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers such as sold under the tradenames of Fluorel and Viton;

butyl rubbers;

polyisobutene, such as sold under the tradename Vistanex;

synthetic polyisoprene rubber;

silicone rubbers;

styrene-butadiene rubbers;

tetrafluoroethylene propylene copolymers; and thermoplastic-copolyesters.

Figure 6:
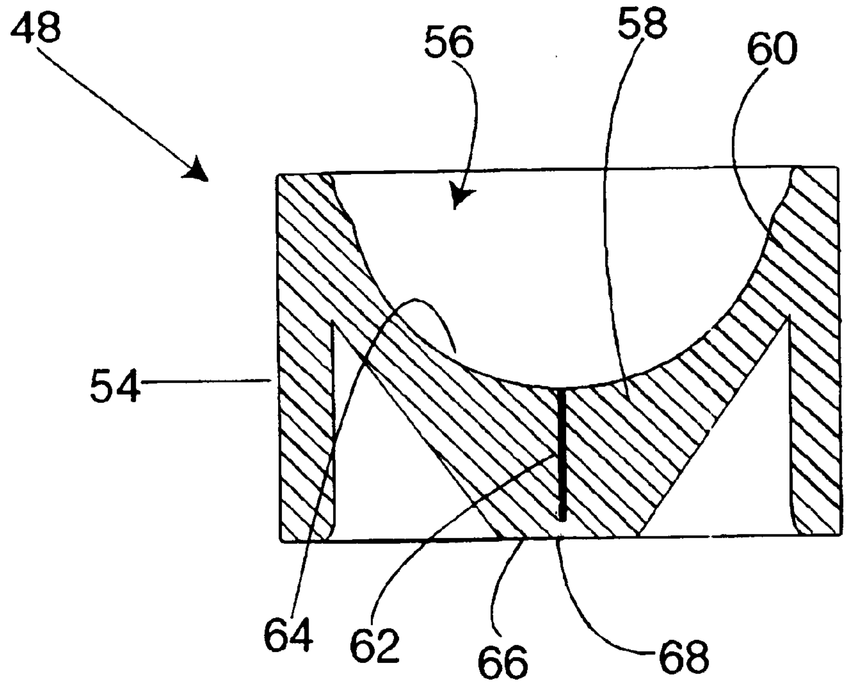
FIG. 6 shows an elastomeric seal in the form of the M-shaped membrane.
Figure 7:
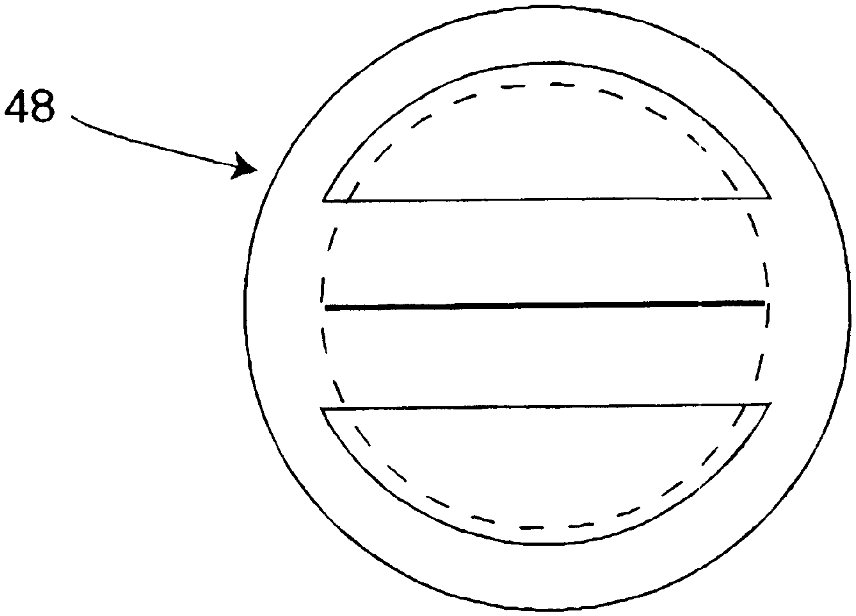
FIG. 7 is a top plan view of the M-shaped membrane shown in FIG. 6.

As best seen in FIGS. 6 and 7, the M-shaped membrane 48 comprises: leg portion 54, and cup-shaped portion 56. Cup-shaped portion comprises: horizontal bottom portion 58; and side portion 60. Leg portion 54 and side portion 60 typically have a thickness of from about 3 to 6 mm while bottom portion 58 typically has a thickness of from about 5 to 20 mm.

The horizontal bottom portion 58 is provided with a slit 62 which extends from the top surface 64 of the horizontal bottom portion toward the bottom surface 66. However, the slit does not penetrate the bottom surface. The unpenetrated membrane, denoted by the numeral 68, has a thickness of from about 0.001 mm to about 2.0 mm. The unpenetrated membrane maintains the content of the container in sealed condition. In use, when this membrane is ruptured by an external access means, such as a luer connector or spike, fluid communication is established between the content of the container and the external access means. Upon disengaging the external access means, the cup-shaped portion of the diaphragm reseals itself for the reason that the membrane is resilient and springs back to its original configuration. As a result, the container is resealed until the fluid withdrawal process is repeated.

The M-shaped membrane is bounded to the medicament-carrying spike 34 at its opening thereof by conventional means known in the art.

Figure 8:
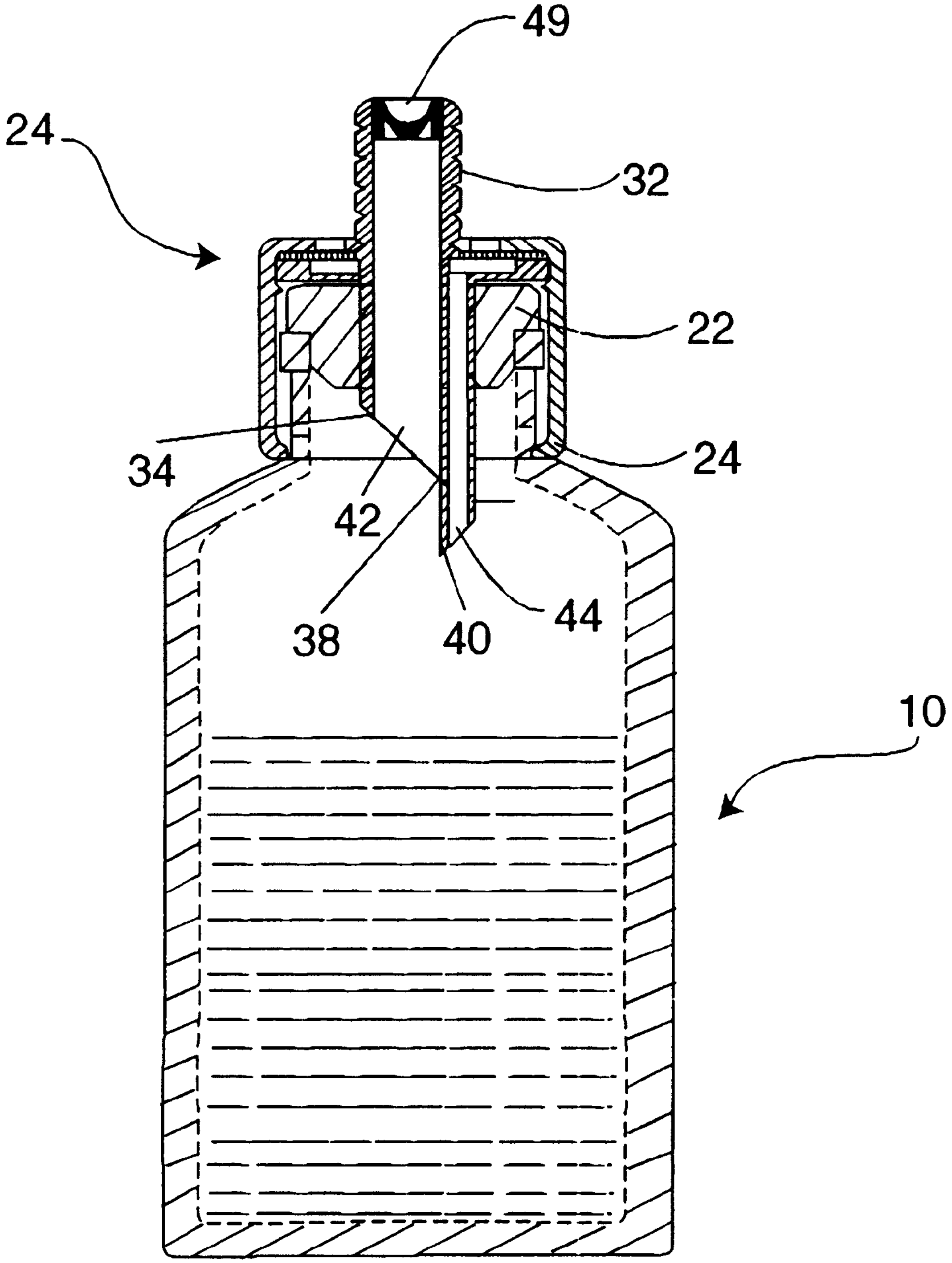
FIG. 8 shows the vial access adapter assembled with the vial.

FIG. 8 shows in cross-sectional view the vial access adapter 24 and the vial 10 assembly. Dual spikes 34 and 36 have been inserted into the vial through stopper 22.Liquid medicament passage 42 just clears the bottom portion of the stopper so that, when the assembly is turned upside-down, essentially all the liquid medicament may be withdrawn from the vial.

Spike 36 having air-flow passage 44 therein is longer than spike 34 having liquid medicament flow passage 42 therein in order to prevent air from circulating back into the liquid medicament flow passage during withdrawal of the liquid medicament from the vial.

Figure 9:
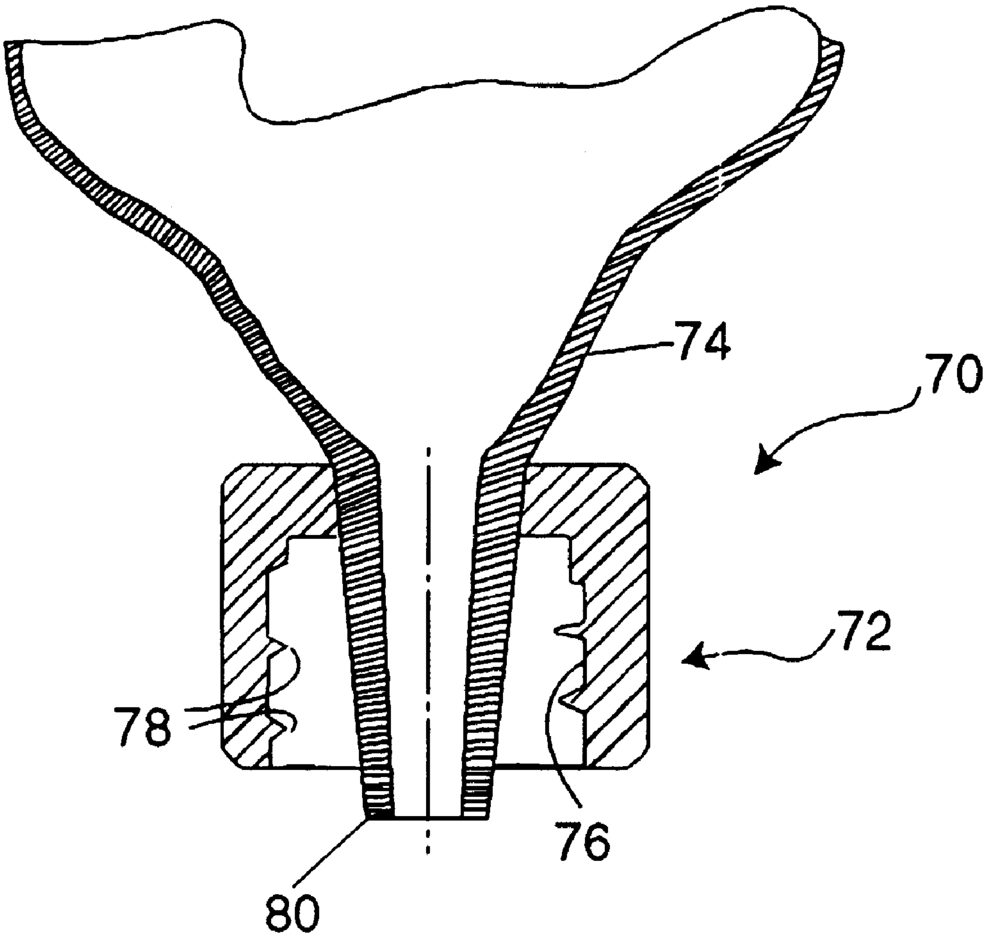
FIG. 9 illustrates a luer connector attachable to the vial access adapter.

FIG. 9 shows in cross-sectional view a typical luer connector 70 attachable to the vial access adapter of the present invention. The luer connector comprises a cylindrical cap 72 and a tubing conduit 74. Cylindrical cap 72 comprises inside wall 76 having threads 78 therein extending towards tubing conduit 74. Upon attachment, luer connector 70 will engage thread means 32 of vial access adapter 24. Tubing conduit 74 has a bottom portion 80 which extends beyond the cylindrical cap and is adapted to rupture the elastomeric membrane 48 or 49 of the vial access adapter 24.

Figure 10:
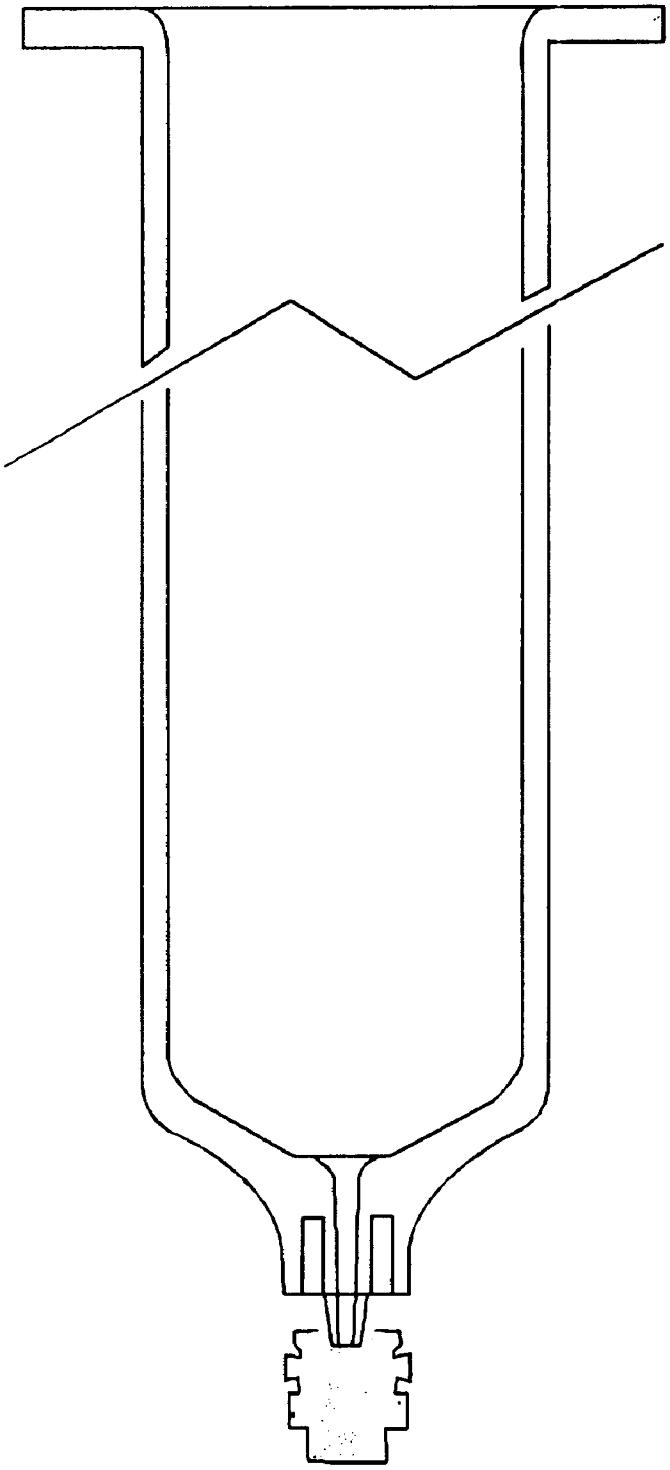
FIG. 10 illustrates, in a cross-sectional view, a portion of the threaded luer connector prior to penetration of a membrane by the luer connector of a syringe.

FIG. 10 shows in cross-sectional view a portion of the threaded luer connector means with the elastomeric membrane therein prior to penetration of the membrane by the luer connector of a syringe.

Figure 11:
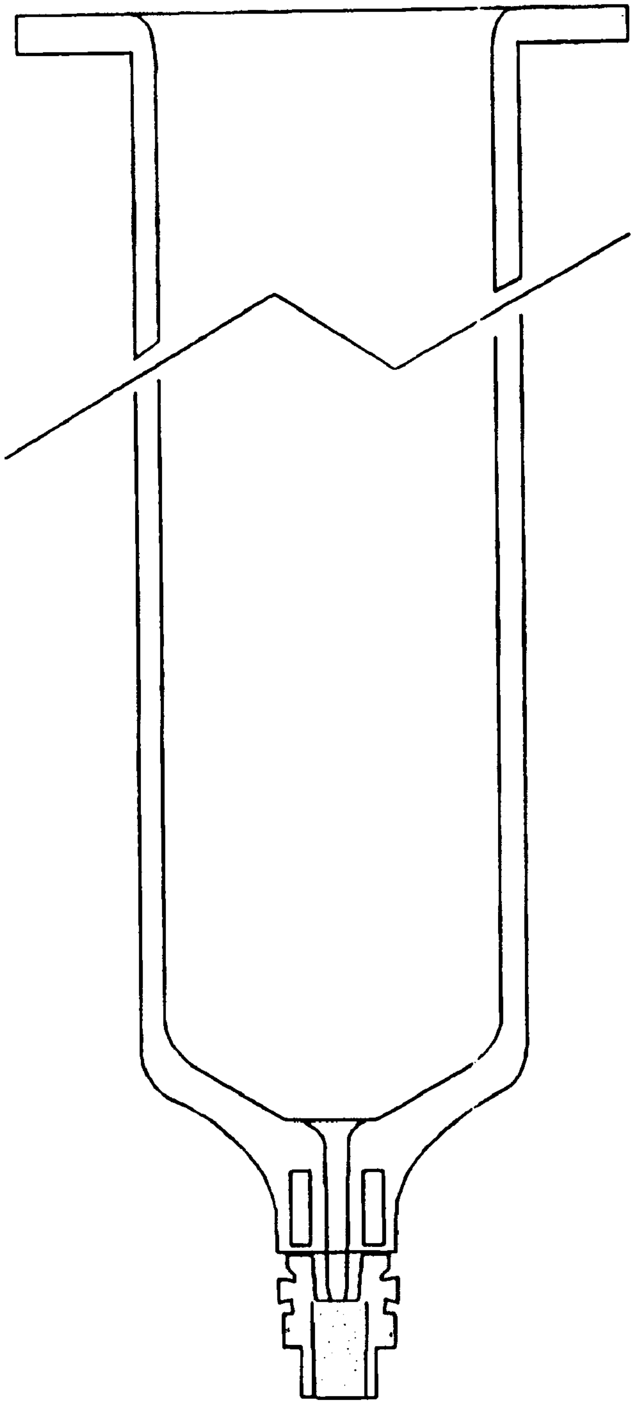
FIG. 11 illustrates, in a cross-sectional view, a portion of the threaded luer connector during penetration and breakthrough of the membrane by the luer connector of the syringe.

FIG. 11 shows in cross-sectional view a portion of the threaded luer connector means with the elastomeric membrane therein during penetration and break-through of the membrane by the luer connector of a syringe.

In use, the vial access adapter is engaged with a vial containing a liquid medicament therein by a snap-on motion. The dual spike penetrates the stopper establishing fluid communication between the vial and the vial access adapter. Next, an external connector or the luer connector of a syringe is engaged with the vial access adapter by a twisting motion, threading the luer connector into the luer connector means of the vial access adapter. Upon sufficient twisting the elastomeric membrane is ruptured and fluid communication is achieved between the luer connector and the vial access adapter. These steps of engagement are accomplished while the vial containing the liquid medicament is positioned on a flat surface in a rightside-up position. Upon completing these steps, the vial is turned upside-down and the liquid medicament is transferred from the vial into the external luer connector having tubing conduit therein from which the medicament is administered to a patient. When a syringe, having a plunger therein equipped with a luer connector is used, withdrawal of the liquid medicament is accomplished by moving the plunger towards its open end and thereby drawing the liquid medicament into the syringe barrel. The desired amount of liquid medicament withdrawn can be seen in the syringe. Upon disconnecting the external luer connector from the vial access adapter, the M-shaped elastomeric membrane reseals itself thereby keeping the liquid medicament in the vial in aseptic condition. The self-sealing membrane allows repeated access to the liquid medicament contained in the vial.

The vial access adapter body is made of rigid or semi-rigid polymeric materials and can be used on bottles and vials made of glass or rigid or semi-rigid polymeric materials. The liquid medicament contained in the bottles and vials can be a therapeutic, a diagnostic, or a nutritional preparation.

LIST OF REFERENCE NUMBERS USED

| | |
|---|---|
| Vial | 10 |
| Cylindrical side wall of vial | 12 |
| Flat bottom portion of vial | 14 |
| Neck portion of vial | 16 |
| Rim portion of top of vial | 18 |
| Open area of top portion of vial | 20 |
| Stopper | 22 |
| Vial access adapter | 24 |
| Cylindrical side wall of vial access adapter | 26 |
| Rim of cylindrical side wall | 27 |
| Flat horizontal top wall of vial access adapter | 28 |
| Protuberance on rim portion | 29 |
| Vent holes in top wall of vial access adapter | 30 |
| Threaded luer connector means | 32 |
| Dual spikes | 34 and 36 |
| Sharp points in dual spikes | 38 and 40 |
| Flow passages in dual spikes | 42 and 44 |
| Slots in cylindrical side wall | 46 |
| Elastomeric seal/membrane, M-shaped diaphragm | 48 |
| U-shaped diaphragm | 49 |
| Internal second wall | 50 |
| Chamber | 51 |
| Filter | 52 |
| Leg portion of M-shaped membrane | 54 |
| Cup-shaped portion of M-shaped membrane | 56 |
| Horizontal bottom portion of cup-shaped portion | 58 |
| Side portion of cup-shaped portion | 60 |
| Slit in bottom portion | 62 |
| Top surface of cup-shaped portion | 64 |
| Bottom surface of cup-shaped portion | 66 |
| Unpenetrated portion of membrane | 68 |
| Luer connector (external) | 70 |
| Cylindrical cap of luer connector | 72 |
| Tubing conduit of luer connetor | 74 |
| Inside wall of cylindrical cap | 76 |
| Threads on inside wall of cylindrical cap | 78 |
| Bottom end portion of tubing conduit | 80 |

Various modifications of the present invention disclosed will become apparent to those skilled in the art. This invention is intended to include such modifications to be limited only by the scope of the claims.

What is claimed is:

1. A vial access adapter-vial assembly comprising:

a) a vial having a medical fluid therein; and b) a vial access adapter body, wherein said vial comprises a fluid port closed by an elastomeric stopper for hermetically sealing the medical fluid contained therein, said elastomeric stopper having a top surface and a bottom surface;

said vial access adapter body comprising:

a horizontal top wall having a plurality of vent holes therein;

a horizontal second wall spaced parallel from said horizontal top wall;

a cylindrical side wall enclosing a chamber between said horizontal top wall and said horizontal second wall and extending downward from said horizontal second wall forming a skirt and terminating in a bottom rim, wherein said chamber contains an anti-bacterial filter therein;

a first spike centrally located in said vial access adapter body having: a top portion extending above said horizontal top wall and terminating in an externally threaded luer connector, and a bottom portion extending downward and terminating in a sharp point;

a fluid flow channel in said first spike designed for carrying said medical liquid from said vial;

a second spike positioned parallel to said first spike extending downward from said horizontal second wall and terminating in a sharp point;

an air flow channel in said second spike designed for air flow from said chamber into said vial during withdrawal of said medical liquid from said vial; and an elastomeric membrane within said externally threaded luer connector for sealing the fluid flow channel;

wherein said first spike and said second spike are pierced through said elastomeric stopper to establish fluid communication with said medical fluid contained in said vial and air flow communication from said chamber into said vial.

2. The vial access adapter of claim 1 wherein said elastomeric membrane is of M-shaped configuration capable of flexing under pressure and re-sealing itself after being pierced by an external access means.

3. The vial access adapter of claim 1 wherein said elastomeric membrane has a thickness of from about 5 mm to about 20 mm, and a durometer of from about 25 to about 80 Shore A.

4. The vial access adapter of claim 1 wherein said elastomeric membrane is of an elastomeric material selected from the group consisting of natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene;

tetrafluoroethylene terpolymers;

butyl rubbers;

polyisobutene;

synthetic polyisoprene rubber;

silicone rubbers;

styrene-butadiene rubbers;

tetrafluoroethylene propylene copolymers; and thermoplastic-copolyesters.

5. The vial access adapter of claim 2 wherein said M-shaped elastomeric membrane comprises a leg portion and a cup-shaped portion.

6. The vial access adapter of claim 5 wherein said cup-shaped portion comprises a horizontal bottom portion having a top surface and a bottom surface and a slit therein extending from the top surface thereof towards the bottom surface thereof without penetrating said bottom surface.

7. The vial access adapter of claim 1 wherein said cup-shaped portion, which is unpenetrated has a thickness of from about 0.001 to about 2.0 mm.

8. The vial access adapter-vial assembly of claim 1 wherein said sharp point of said first spike piercing said elastomeric stopper is essentially at the bottom surface of said elastomeric stopper.

9. The vial access adapter-vial assembly of claim 1 wherein said anti-bacterial filter is a circular mat of randomly oriented fibers bound together with a polymeric material selected from the group consisting of polyester elastomers, ethylene methacrylate, ethylene vinyl acetate, ethylene vinyl alcohol, polyethylene and polypropylene treated with an anti-bacterial agent.

10. The vial access adapter-vial assembly of claim 1 wherein said randomly oriented fibers are selected from the group consisting of nylon, cellulose rayon and polyester.

* * * * *